(12) United States Patent
Kroll et al.

(10) Patent No.: US 6,387,038 B1
(45) Date of Patent: May 14, 2002

(54) AIR CELL MOUNTABLE SUPPORT SHAFT

(75) Inventors: Kai Kroll, Minneapolis; Scott C. Meyerson, Moundsview, both of MN (US)

(73) Assignee: St. Croix Medical, Inc., Minneapolis, MN (US)

( * ) Notice: Subject to any disclaimer, the term of this patent is extended or adjusted under 35 U.S.C. 154(b) by 0 days.

(21) Appl. No.: 09/498,157

(22) Filed: Feb. 4, 2000

Related U.S. Application Data

(60) Provisional application No. 60/118,858, filed on Feb. 5, 1999.

(51) Int. Cl.$^7$ .............................. H04R 25/00; A61F 2/18
(52) U.S. Cl. ............................................ 600/25; 623/10
(58) Field of Search .................. 128/785; 222/195; 433/173; 600/25; 623/10; 411/11, 5, 16

(56) References Cited

U.S. PATENT DOCUMENTS

| | | | | |
|---|---|---|---|---|
| 4,487,210 A | * | 12/1984 | Knudsen et al. ............ 128/785 |
| 4,662,543 A | * | 5/1987 | Solimar ....................... 222/195 |
| 4,774,933 A | * | 10/1988 | Hough et al. ................. 600/25 |
| 5,015,224 A | * | 5/1991 | Maniglia ...................... 433/25 |
| 5,195,891 A | * | 3/1993 | Sulc ............................ 433/173 |
| 6,001,129 A | * | 12/1999 | Bushek et al. ................ 623/10 |

* cited by examiner

*Primary Examiner*—Eric F. Winakur
*Assistant Examiner*—Nikita R Veniaminov
(74) *Attorney, Agent, or Firm*—Fredrikson & Byron, P.A.

(57) ABSTRACT

A support shaft for use in supporting a universal connector for use in an implantable hearing assistance system. The support shaft provides an implantation surgeon with several features designed to secure a support shaft within the air cell-filled portion of a temporal bone. The support shaft is further configured to allow the secure attachment of the universal connector, the connector configured to support transducers and other components of an implantable hearing assistance system.

16 Claims, 5 Drawing Sheets

FIG. 3.1

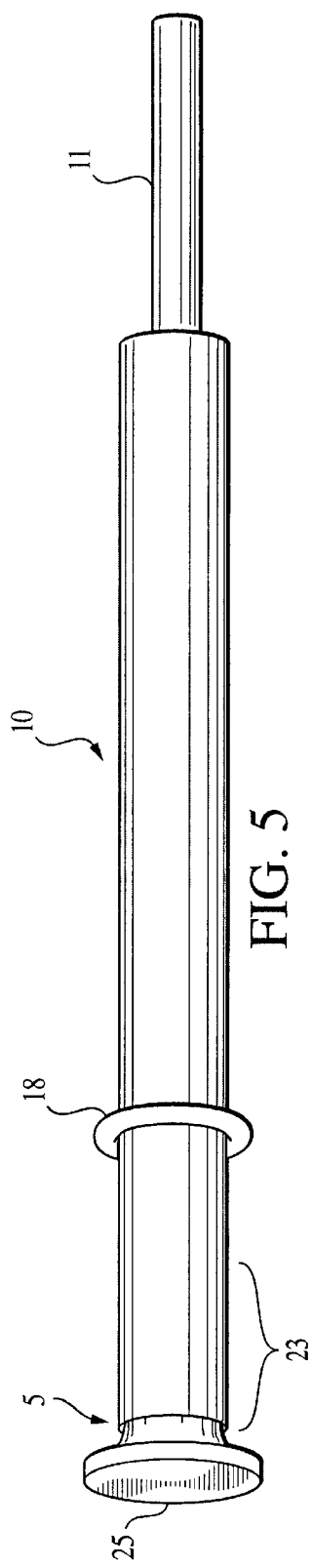
FIG. 5
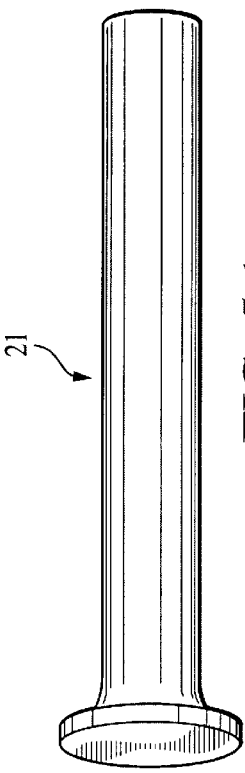
FIG. 5.1
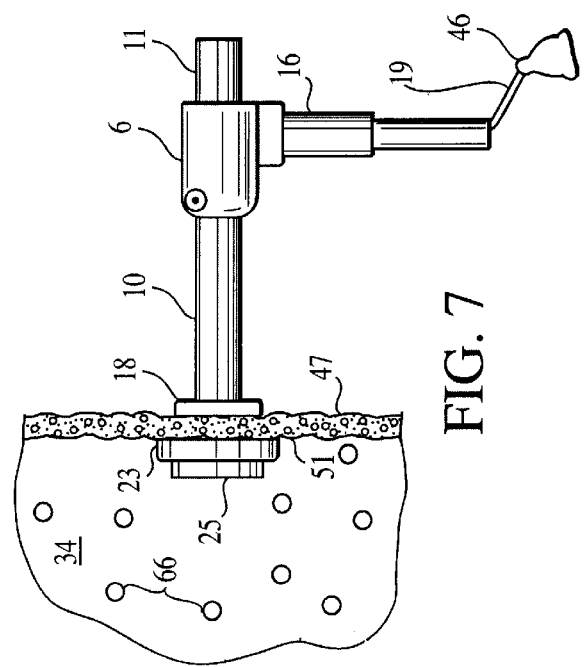
FIG. 7
FIG. 6

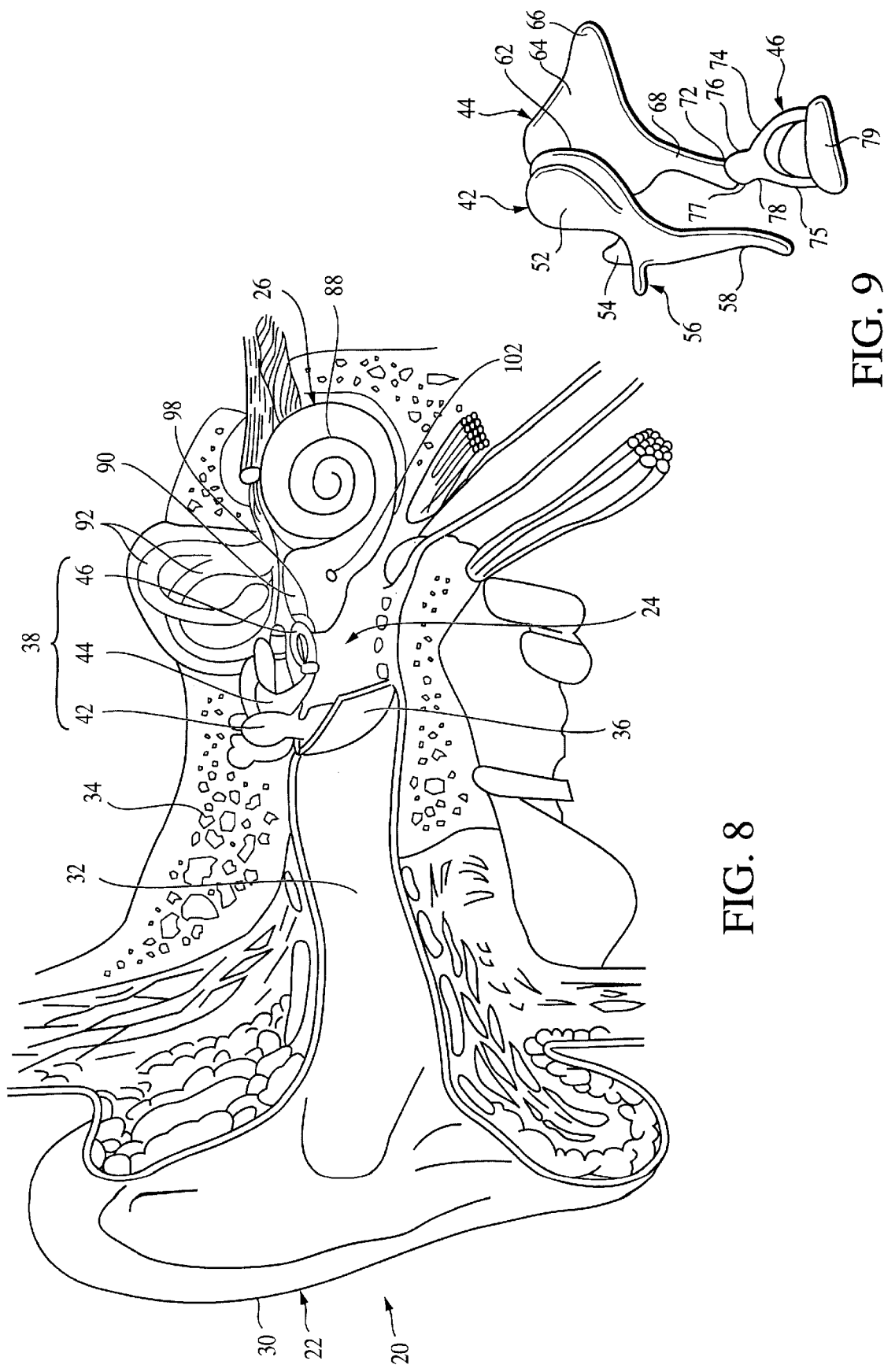

AIR CELL MOUNTABLE SUPPORT SHAFT

This Appln claims benefit of Prov. No. 60/118,858 filed Feb. 5, 1999.

BACKGROUND OF THE INVENTION

1. Field of the Invention

This invention relates to implantable hearing assistance devices and components thereof.

2. Description of Related Art

Field of implantable hearing assistance systems presents many challenges, not the least of which is the small physical size of some implantation regions. It is desirable to make the components of any implantable hearing assistance system as small as possible, to fit into the limited space of the implantation area, yet adaptable to allow for the various surgical and natural morphological differences found at the site of implantation.

In some types of implantable hearing aid systems, transducers located within the middle ear engage one or more auditory elements and transduced mechanical vibrations into electrical signals, and vice versa. Typically, electrical signals are amplified and transmitted to an electromechanical output transducer, which in turn vibrates a bone in the ossicular chain of the middle ear by translating the amplified electrical signal.

In those types of implantable hearing assistance systems that require transducers to be implanted within the middle ear, surgical access to the middle ear must be obtained. This surgical procedure is called a basic or simple mastoidectomy. The basic mastoidectomy procedure is not a procedure that is performed in the same manner by surgeons throughout the world. Typically, in the United States, a surgeon might perform a typical or basic mastoidectomy using a wide saucerization technique and would typically remove a large portion of the air cells found within the mastoid bone region, typically around the main trunk of the facial nerve and around the mastoid tip area. The removal of these air cells is performed to uncover more solid bone, without air cells, to form a good foundation onto which to mount transducers or transducer support members.

In other parts of the world, for example Germany, it is not typical for a surgeon who is performing the basic or typical mastoidectomy to remove a large amount of the air cells found in the mastoid bone. Thus, for surgeons who would prefer to leave a good portion of the mastoid bone containing the air cells intact and still desire to implant transducers and other components of an implantable hearing assistance system within the middle ear of a hearing-impaired patient, there is a dilemma of finding a solid foundation into which transducers or transducer support members can be attached.

It is therefore an object of this invention to provide a support shaft, configured to accept a universal connector for mounting transducers and related components that can be mounted within the mastoid bone containing air cells.

SUMMARY OF THE INVENTION

The invention presented relates to components of an implantable hearing assistance system. More specifically, the invention presented is a support shaft configured to receive a universal connector for holding transducers and related components of an implantable hearing assistance system on a first end, and apparatus disposed on a second end of the support shaft to facilitate the mounting of the support shaft in the mastoid bone that contains air cells.

BRIEF DESCRIPTION OF THE DRAWINGS

FIG. 3.1 is a front view of the retaining washer showing the additional bone screw holes.

FIG. 5 is the further embodiment of the subject invention with the pull rod and formal portion of the support shaft.

FIG. 5.1 is a depiction of the pull rod used in the embodiment that is depicted in FIG. 5.

FIG. 6 illustrates the universal connector and attached sleeve and transducer.

FIG. 7 is a depiction of the embodiment of FIG. 5 attached to the mastoid bone that has air cells.

FIG. 8 illustrates the cross-section of a generally anatomically normal human ear.

FIG. 9 depicts the bones of the ossicular chain.

DETAILED DESCRIPTION OF PREFERRED EMBODIMENTS

Figure 1:
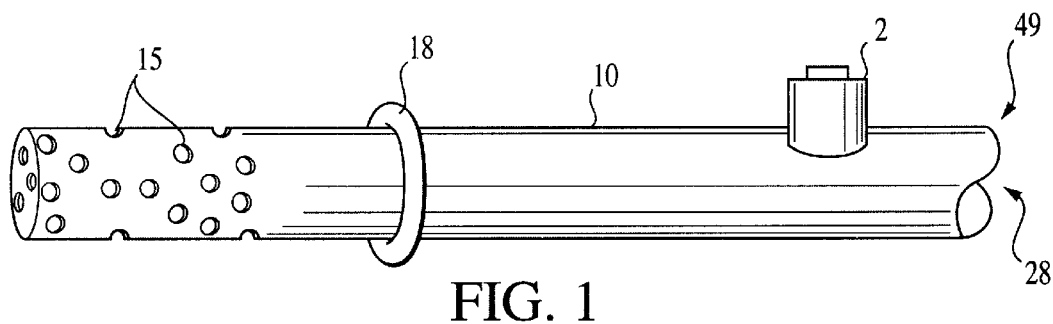
FIG. 1 depicts an embodiment of the support shaft configured to accept an injection of biocompatible adhesive.

Referring to FIG. 8, ear 20 includes outer ear 22, middle ear 24, and inner ear 26. Outer ear 22, in turn, includes pinna 30 and exterior auditory canal (external acoustic meatus) 32. The exterior auditory canal extends through mastoid 34.

Middle ear 24 begins at tympanic membrane 36, the interior terminus of exterior auditory canal 32, and includes tympanic membrane 36 and ossicular chain 38. Ossicular chain 38, in turn, includes malleus 42, incus 44, and stapes 46.

FIG. 8 illustrates a frontal section of a human ear. Sound waves are directed into external auditory canal 32 by pinna 30. Frequency characteristics of the sound waves are preferably modified by the resident characteristics of external auditory canal 32. The sound waves impinge upon tympanic membrane 36, interposed at the terminus of external auditory canal 32, thereby producing mechanical tympanic vibrations. The mechanical energy of the tympanic vibrations is communicated by a series of articulating bones located in middle ear 24 to inner ear 26, comprising cochlea 88, vestibule 90, and semicircular canals 92. The series of articulating bones is referred to generally as ossicular chain 38. Thus, tympanic membrane 36 transforms acoustic energy in external auditory canal 32 to mechanical energy and ossicular chain 38 conveys the mechanical energy to cochlea 88. The hearing aid system comprising this invention assists the human auditory system in converting acoustic energy contained within sound waves into electrochemical signals delivered to the brain and interpreted as sound.

As best seen from FIG. 9, malleus 42 includes head 52, lateral process 54, anterior process 56, and manubrium 58.

Malleus 42 attaches to tympanic membrane 36 at manubrium 58. Incus 44 articulates with malleus 42 at incudomalleolar joint 62 and includes body 64, short crus 66, and long crus 68. Stapes 46 articulates with incus 44 at incudostapedial joint 72 and includes posterior crus 74, anterior crus 75, capitulum 76, and base (front plate) 79. Capitulum 76 of stapes 46, in turn, includes head 77 and neck 78.

Base 79 of stapes 46 is disposed in and against a portion of inner ear 26. Inner ear 26 includes cochlea 88, vestibule 90, and semicircular canals 92. Base 79 of stapes 46 attaches to a membrane covered opening between cochlea 88 and middle ear 24 referred to as oval window 98. Oval window 98 is considered part of cochlea 88.

Normally, prior to implantation of the invention, tympanic vibrations are mechanically conducted through malleus 42, incus 44, and stapes 46 to oval window 98. Vibrations at oval window 98 are conducted into the fluid-filled cochlea 88. Pressure is generated in cochlea 88 by fluidic motion accompanied by a second membrane covered opening in cochlea 88. The second membrane covered opening between cochlea 88 and middle ear 24 is referred to as round window 102. Round window 102 is also considered part of cochlea 88. Receptor cells in cochlea 88 translate the fluidic motion into neural impulses which are transmitted to the brain and perceived as sound. However, various disorders of tympanic membrane 36, ossicular chain 38, and/or cochlea 88 can disrupt or impair normal hearing.

For example, hearing loss due to damage in cochlea 88 is referred to as sensorineural hearing loss. Hearing loss due to an inability to conduct mechanical vibrations through middle ear 24 is referred to as conductive hearing loss. Other problems occur for some patients who have ossicular chains 38 which lack resiliency. Ossicular chains 38 with insufficient resiliency are either inefficient or totally fail to transmit mechanical vibrations between tympanic membrane 36 and oval window 98. As a result, fluidic motion in cochlea 88 is attenuated and receptor cells in cochlea 88 fail to receive adequate mechanical stimulation. Damaged or missing elements of ossicular chain 38, of course, may further interrupt transmission of mechanical vibrations between tympanic membrane 36 and oval window 98.

Various techniques have been developed to remedy hearing loss resulting from conductive or sensorineural hearing loss. For example, tympanoplasty is used to surgically reconstruct tympanic membrane 36 and establish ossicular continuity from tympanic membrane 36 to oval window 98. Various passive mechanical prostheses and implantation techniques have been developed in connection with reconstructive surgery of middle ear 24 for patients with damaged elements of ossicular chain 38. Two basic forms of prostheses are available: total ossicular replacement prosthesis, which is connected between tympanic membrane 36 and oval window 98; and partial ossicular replacement prosthesis, which is positioned between tympanic membrane 36 and stapes 46.

Different types of hearing aids have been developed to compensate for hearing disorders. A conventional "air conduction" hearing aid is sometimes used to overcome hearing loss due to sensorineural cochlear damage or mild conductive impediments to ossicular chain 38. Conventional hearing aids utilize microphones which transduce sound into an electrical signal. Amplification circuitry amplifies the electrical signal. A speaker transduces the amplified electrical signal into acoustic energy transmitted to tympanic membrane 36. In such systems, however, some of the transmitted acoustic energy is typically detected by the microphone, resulting in a feedback signal which degrades sound quality. Conventional hearing aids also often suffer from a significant amount of signal distortion.

Implantable hearing aid systems have also been developed, utilizing various approaches to compensate for hearing disorders. A variety of inner ear and middle ear implantable hearing aid systems have been designed. Implantation of a hearing aid system within the middle ear is particularly advantageous for various reasons. Importantly, placement of the system within the middle ear serves the purpose of shielding the device from damage caused by an impact to the head in general, or the ear specifically. Such a blow may have deleterious effects on the operability of the system or worse, such as when such a blow induces mechanical or vibratory consequences causing damage to one or more components of the inner ear. Another advantage of middle ear implantation is the ability to provide the patient with a system having no external components to address the issue of cosmetic concerns, including the lessening of any feelings of embarrassment or self-consciousness. Other advantages of middle ear implantation exist and can be readily appreciated by one skilled in the art.

A cochlear implant is an electronic device that allows profoundly deaf people to "hear" by electrical stimulation of the auditory nerve fibers within the inner ear. A typical system includes an external microphone, signal processor, and transmitter, and an implanted receiver and electrode. The microphone transponds normal sound waves, converting this mechanical sound energy into electrical energy representative thereof. The processor amplifies the electrical energy, filters it and sends it to the transmitter, which changes the electrical signals into magnetic signals. Transcutaneous magnetic currents cross the skin and are received by the implanted receiver, a coil for example, and the signal travels to the cochlea via a wire electrode. Current flows between this active electrode and a nearby ground electrode, preferably disposed in the Eustachian tube, to stimulate nerve fibers present in the cochlea. The brain interprets this stimulation as sound.

A particularly interesting class of hearing assistance systems includes those that are configured for disposition principally within middle ear 24. In middle ear implantable hearing aids, an electrical-to-mechanical output transducer couples mechanical vibration to ossicular chain 38, which is optionally interrupted to allow coupling of the mechanical vibrations to ossicular chain 38. Both electromagnetic and piezoelectric output transducers have been used to effect mechanical vibrations upon ossicular chain 38.

One example of a partial middle ear implantable hearing aid system having an electromagnetic output transducer comprises: an external microphone transducing sound into electrical signals; external amplification and modulation circuitry; and an external radio frequency (RF) transmitter for transdermal RF communication of an electrical signal. An implanted receiver detects and rectifies the transmitted signal, driving an implanted coil in constant current mode. A resulting magnetic field from the implanted drive coil vibrates an implanted magnet that is permanently affixed only to incus 44. Such electromagnetic output transducers have relatively high power consumption, which severely limits their usefulness in total middle ear implantable hearing aid systems.

A piezoelectric output transducer is also capable of affecting mechanical vibrations to ossicular chain 38. An example of such a device is disclosed in U.S. Pat. No. 4,729,366, issued to Schaefer. Therein, a mechanical-to-electrical piezoelectric input transducer is associated with malleus 42, transducing mechanical energy into an electrical signal, which is amplified and further processed. A resulting electrical signal is provided to an electrical-to-mechanical piezoelectric output transducer that generates a mechanical vibration coupled to a separate element of ossicular chain 38 or to oval window 98 or round window 102. Ossicular chain 38 is interrupted by removal of incus 44. Removal of part of the ossicular chain prevents the mechanical vibrations delivered by the piezoelectric output transducer from mechanically feeding back to the piezoelectric input transducer.

Piezoelectric transducers have several advantages over electromagnetic transducers. The smaller size of the piezoelectric transducer advantageously eases implantation into middle ear 24. The lower power consumption of the piezoelectric transducer is particularly attractive for total middle ear implantation hearing aid systems, which may include a limited-longevity implanted battery as a power source.

A piezoelectric transducer is typically implemented as a ceramic piezoelectric bi-element transducer, which is frequently a cantilevered double-plate ceramic element in which two plates are bonded together such that they amplify a piezoelectric action in a direction approximately normal to the bonding plane. Such a bi-element transducer vibrates according to a potential difference applied between two bonded plates. A proximal end of such a bi-element transducer is typically cantilevered from a transducer mount which is secured at a reference point to a non-ossicular chain bone within the middle ear. A distal end of such a bi-element transducer couples mechanical vibrations to an ossicular element such as stapes 46.

Securing a bi-element transducer mount to the temporal bone adds invasive complexity to the surgical implantation procedure. Given the delicate nature of the middle ear, placement of the system at its proper position and with the appropriate level of pressure on the auditory element is critical. Failure to account for small dimensional anatomical variations among patients can have considerable consequences, supplying the difference between acceptable and poor hearing ability for a patient. Although piezoelectric transducers provide many advantages, the invention contemplates use of other types (e.g., electromechanical) of transducers.

Implantation of components of an implantable or partially implantable hearing assistance system typically involves gaining physical access to middle ear 24. This access is necessary for the purpose of implanting the transducers. These transducers can be sensors, drivers, microphones, or other components. Sensors and drivers commonly contact at least one of the bones of ossicular chain 38 within middle ear 24. The contact must be secure to insure that during the life of the hearing assistance system, appropriate physical contact is maintained between the transducer and the bone. Thus, the anchoring of a transducer within middle ear 24 is vital to the operation of this type of hearing assistance system. If physical contact between the target bone and the transducer is either lost or sporadic, the hearing assistance system cannot perform adequately. This poses a challenge for the surgeon, created not only by the surgical procedure, but by the anatomical differences found among patients. Because of both surgically created and naturally occurring morphological variations likely to be encountered within any given implantation area, flexibility and adaptability in the mounting and adjusting of the transducer is important for safe and effective implantation.

The surgical procedure commonly used to gain physical access to middle ear 24 is called a basic or simple mastoidectomy. Because this procedure gives only limited access to middle ear 24, it is common to follow the mastoidectomy with a procedure to further open facial recess 15. These procedures are performed with various surgical tools, which include a burr and/or a diamond burr. A burr is a spherical boring instrument (not shown) that removes bone and bony structures. As can be appreciated, the shape of the instrument dictates the shape of the area of the bone that remains after bone is removed. Often the mastoidectomy commences with the largest burr available. As the implantation area becomes smaller, the burr size decreases accordingly. A diamond burr is used for fine removal of anatomical structure. The use of different sized burrs creates layers of bone with a series of concave layers, with the shape of each layer generally dependent upon the size and shape of the burr used.

The mastoidectomy is initially performed with a large cutting burr, as well as suction, irrigation and other devices. The size of the burr typically decreases as depth into the mastoid bowl increases. During the initial steps of the procedure, the primary goal is to identify landmarks that allow the surgeon to maintain orientation while drilling. An initial cut with the burr is normally made along the temporal line while a subsequent cut is made substantially perpendicular to the first cut, and toward the mastoid tip. These two lines intersect just posterior to the spine of Henle. Initially, this region, called the supra medial triangle of Macewen, is the deepest part of the dissection and actually overlies the mastoid atrium. Using these first two cuts with the burr as general boundaries, the mastoid cortex bone is then removed in a systematic fashion referred to as saucerization. Saucerization of the cortex continues while landmarks are identified to maintain orientation. Wide saucerization is important in this procedure because insufficiently wide saucerization may result in inadequate recognition of landmarks and thus perhaps a less desirable exposure to the implantation area upon deeper dissection. It is this initial wide saucerization, followed by the narrowing of the dissection area, that creates one of the many challenges faced by the surgeon in mounting transducers and transducer support brackets, and which contributes to the need for minimizing any further tissue trauma beyond that necessary.

Important landmarks that the surgeon is looking for, during progressive cavity saucerization, are posterior bony canal wall, tegman, and sigmoid sinus. Care must be taken in this region because of the presence of the facial nerve. Typically, digastic ridge is identified and preserved as a landmark to the facial nerve. The facial nerve lies roughly on a line between the anterior tip of the digastic ridge and the lateral extent of the horizontal canal. In normal anatomy, the facial nerve lies directly inferior and medial to the fossa incudis as it finishes its tympanic segment. Once the facial nerve is identified, the air cells near the facial nerve can be safely removed with the smaller-sized diamond burr.

Mastoid 34 contains air cells that will be encountered during the dissection. The air cells, as mentioned above, are also typically present in the area of the facial nerve, as well as in other areas of the dissection. In some countries, the above-described procedure typically attempts to achieve the removal of all, or a significant amount of, the air cells so that a more firm bony structure is revealed. The more firm bony structure is a preferred mounting area for a transducer, or transducer support member. However, in other areas of the world, removal of a significant amount of the air cells of mastoid 34 are not typically effected during the simple mastoidectomy, resulting in further challenges to finding a secure mounting site. The increase in the challenge presented by the technique of leaving a significant portion of the air cells in the mastoid bone, typically around the mastoid tip, is a result of the weaker support structure represented by the mastoid bone when it is filled with air cells. The air cells themselves represent pockets of air within the mastoid bone, which weakens the overall structure of the bone. Because some surgeons feel that it is less intrusive to leave as much of the mastoid bone intact as is possible and still gain access to the middle ear for implantation, much of the mastoid air cells are left intact, specifically in the mastoid tip area. It will be recognized by those skilled in the art that this invention will have application beyond the use of monitoring in air cell-filled regions of the mastoid bone. Any fixation site, where the site is not as stable as desired, will benefit from the invention provided.

The variable surgically created shape of the implantation area, as well as the limited number of available implantation sites also requires flexibility on the part of the surgeon, as well to anchor a transducer or transducer support member within the site, based upon the condition of the bone found at the implantation site, among other factors, pose further challenges.

If the mounting of the transducer or support members thereof are to be completed successfully, the surgeon must be able to adapt to the conditions as discovered or created within the implantation area. It is this challenge that the various embodiments of the present invention address.

The present invention provides support shaft 10, and a method, for mounting a support shaft within the air cells of the mastoid bone in the middle ear region of a hearing-impaired patient. One embodiment of the invention facilitates mounting to the air cell-filled regions of the mastoid bone. In this embodiment, support shaft 10 is configured to receive universal connector 6 onto which sleeve 16 for supporting transducer 19 can be attached. When reference is made in this application to transducer 19, it should be recognized that transducer 19 may be a driver (an output transducer), or a sensor (an input transducer), or other similarly functioning device.

Figure 2:
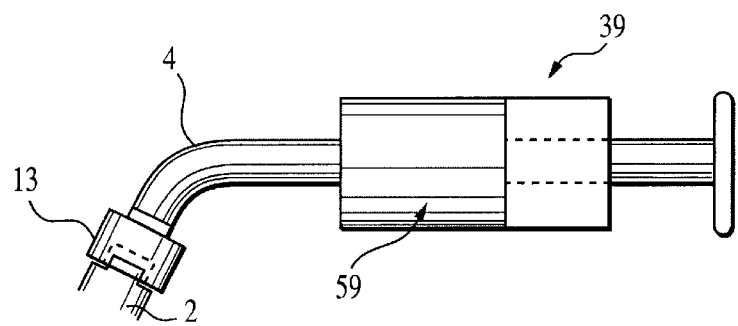
FIG. 2 is a depiction of an embodiment of an adhesive pump attachable to the support shaft embodiment of FIG. 1.

One preferred embodiment of the subject invention appears in FIG. 1. FIG. 1 depicts support shaft 10 defining axial bore 28 that runs the length of support shaft 10. During the implantation surgery, the surgeon will, after determining the approximate area for implantation, drill an aperture in the mastoid bone region containing the air cells, the drilled hole being only slightly larger in diameter than the diameter of shaft 10. Shaft 10 is then inserted into the aperture created by the surgeon to a predetermined depth, or in those embodiments where shaft stop 18 is used, until stop shaft 18 engages the outer surface of the implantation region 47. In this embodiment of the invention, first end 49 is closed and the other end is at least partially restricted. A biocompatible adhesive is then injected through fitting 2 into bore 28, defined by support shaft 10. When sufficient amounts of adhesive have been injected into support shaft 10, the biocompatible adhesive will exit support shaft 10 through a plurality of apertures 15, located distal to shaft stop 18. When the biocompatible adhesive exits the plurality of apertures 15, it will flow in and around support shaft 10 and further flow into air cells 66 exposed to support shaft 10 within mastoid bone 34. The exit end and size and placement of the apertures will be configured so that the adhesive tends to be disposed in and around the support. Once the biocompatible adhesive has cured, a stable foundation will have been created. FIG. 2 depicts adhesive pump 39. The adhesive pump comprises adhesive reservoir 59, flexible hose 4, and fitting coupling 13 configured to couple with fitting 2 for the injection of a biocompatible adhesive. Specially-adapted syringes, dual-barreled syringes, and other devices known to those familiar with the use of medical adhesives can be used to deliver the adhesive to the support via the fitting 2 that accepts standard adapters, e.g., Luer-locks™. These pumps can be controlled manually or automatically to maintain pump rates and pressures so that fracture strength of the bone is not exceeded. Once the biocompatible adhesive has cured, a stable foundation will have been created. An advantage of this embodiment is that the adhesive will interpenetrate the bony network of the air cells, the drilled hole, and the apertures to form a solid interlocking network so that the anchorage of the support shaft will be as strong as the strength of the adhesive and sufficient even if adhesion between the adhesive and support shaft or bone is poor. Furthermore, the volume of the adhesive can be adjusted to control the size of the adhesive bolus so that force applied against the support shaft will be distributed across a larger area of bone than if a simple mount were used, e.g., a self-tapping screw.

Figure 3:
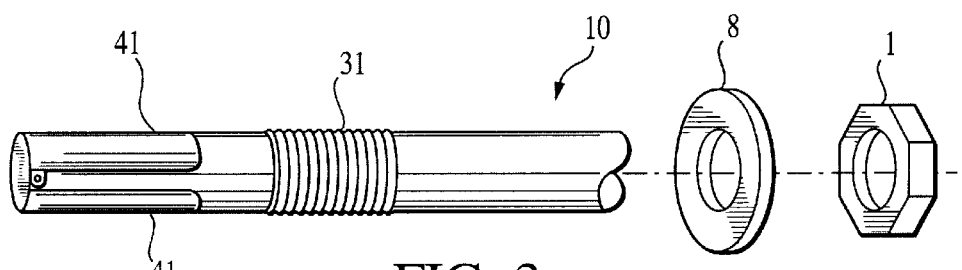
FIG. 3 is a depiction of another embodiment of the subject invention using wings as a retaining washer and retainer nut as the retaining means.
Figure 4:
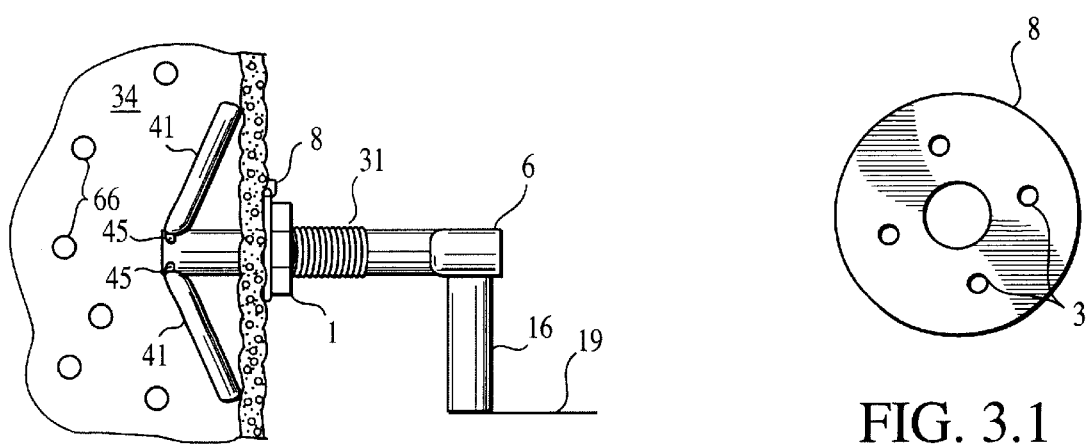
FIG. 4 shows the embodiment of FIG. 3 attached to mastoid bone.

FIG. 3 is another preferred embodiment of the provided invention. This preferred embodiment uses wings 41 configured to engage an inner surface of air-filled mastoid bone region 51. Wings 41 are configured to conform to the cylindrical shape of shaft 10 when unextended. Wings 41 are pivotably connected to shaft 10 at region 45. Wings 41 are free to move at an angle, substantially 90 degrees from support shaft 10. The embodiment depicted in FIG. 3 further includes threaded portion 31 on the outer circumference of support shaft 10 configured to engage with retaining nut 1. Retaining washer 8 which defines a bore substantially equal to diameter support shaft 10, function to further distribute the force, exerted by retaining nut 1, against the outer surface of the mastoid bone containing the air cells 47. FIG. 3.1 is a head-on view of retaining washer 8 showing additional retaining means in the form of further apertures. These apertures can be used as bone screw holes, staple holes, or any other retaining means known by those skilled in the art. The embodiment of the provided invention depicted in FIG. 3 is also inserted into an aperture drilled by the implantation surgeon. The aperture created in the air cell-filled mastoid bone is drilled large enough to accommodate not only support shaft 10 but also wings 41. The aperture is drilled to a depth sufficient to accommodate the full length of the wings so that the wings may be spread to engage the inner surface of the mastoid bone containing air cells 51. Once the wings have been extended to engage the interior surface of mastoid bone 51, either by a spring mechanism or other means known in the art, retaining washer 8 can then be placed upon support shaft 10 to engage the outer surface of mastoid bone region 47 and secured by retaining nut 1. Retaining nut 1 is screwed down upon retaining washer 8, forming a compressive connection with partially-extended wings 41, thereby securing support shaft 10 within mastoid bone 34. Once surface support shaft 10 is securely anchored within the air cell-filled mastoid bone, universal connector 6 can be securely fastened to the first end of support shaft 49. Subsequently, sleeve 16, with attached transducer 19, can be then attached to the universal connector, and adjustment of transducer 19 against stapes 46, or other auditory elements located within the inner ear, can proceed. Thus, embodiments of the invention provide an anchor similar to what might be used in the housing industry to support an object on a hollow walled structure.

Figure 10:
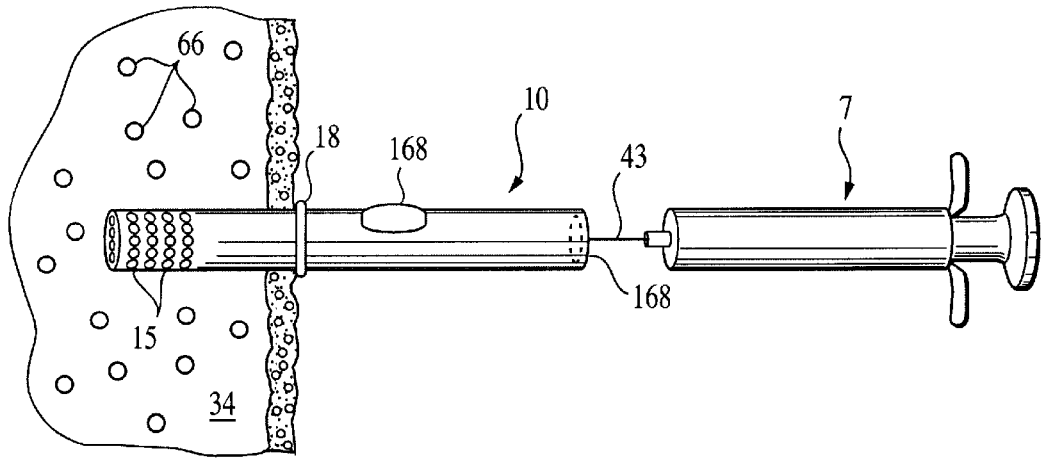
FIG. 10 is a depiction of another embodiment of the support shaft configured to accept an injection of biocompatible adhesive shown with the resilient plug configuration shown inserted into the air cell portion of a mastoid bone.
Figure 11:
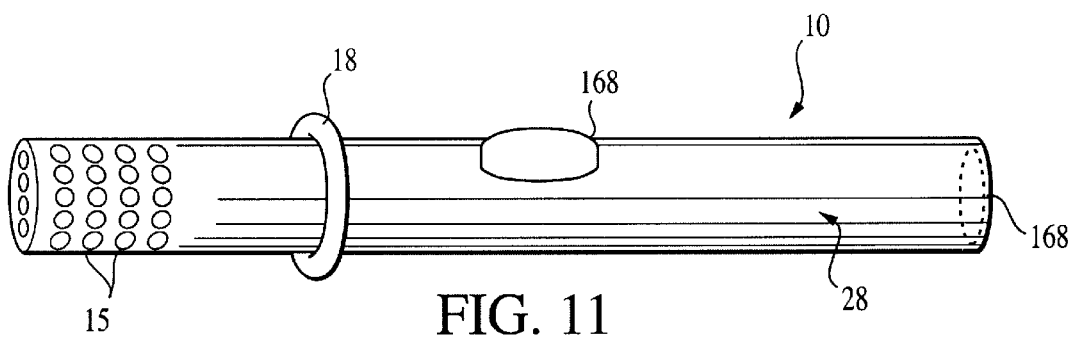
FIG. 11 is a further depiction of the FIG. 10 embodiment.

Another embodiment of support shaft 10 is represented in FIG. 10. This embodiment does not use fitting 2, but instead uses advantageously located resilient plugs 168 as a conduit for injecting biocompatible adhesive into axial bore 28 of support shaft 10. Resilient plug 168 can be located in a variety of areas on support shaft 10, including at the first end of support shaft 10, and throughout the outer circumference of support shaft 10. Some of these described placements of the resilient plug 168 are depicted in FIG. 10. FIG. 10 also depicts the means by which biocompatible adhesive can be injected into support shaft 10. A non-coring needle 43 attached to an adhesive pump or syringe 7, syringe 7 being filled with biocompatible adhesive, can be injected directly into axial bore 28 of support shaft 10. As in a manner similar to that with the use of adhesive pump 39, the embodiment described above and depicted in FIG. 1, biocompatible adhesive is injected until sufficient amounts of biocompatible adhesive flow out of the plurality of apertures located generally at the second end of support shaft 10 until the air cell-filled region 66 of mastoid bone 34 becomes sufficiently pervaded by the biocompatible adhesive. The advantageous placement of resilient plug 168 on various surfaces of support shaft 10 allows for the implantation surgeon to gain access to support shaft 10, for injection of the biocompatible adhesive, from a variety of angles, particularly when used in conjunction with a curved needle. Because of the varying nature of the mastoid surgery, and the surgically and naturally created morphological differences that are typically found at the site of implantation, the ability of the implantation surgeon to gain access to support shaft 10 from a number of different perspectives for injecting of the biocompatible adhesive, is an advantageous element of the invention.

In FIG. 5, another embodiment of support shaft 10 is depicted. In this embodiment, support shaft 10 is defined by axial bore 28 that is open on both ends. Pull rod 21, which has flared end 25 and stem 11, is configured to fit within bore 28 of support shaft 10. Pull rod 21 is placed within bore 28 of support shaft 10 so that flared end 25 of pull rod 21 engages second end 5 of support shaft 10. In this embodiment, the length of pull rod 21 is such that when flared end 25 of pull rod 21 is inserted as described above, into bore 28 of support shaft 10, stem 11 protrudes past first end 49 of support shaft 10. After support shaft 10 and pull rod 21 have been so assembled, and after the implantation surgeon has drilled the appropriate aperture in the region of the mastoid bone containing the air cells into which the implantation surgeon desires to mount the support shaft, second end 5 of the support shaft is inserted into the aperture until shaft stop 18 contacts the outer surface of mastoid bone 47, preventing further penetration of support shaft 10. Stop shaft 18 is adjustable by the implantation surgeon to accommodate the depth of the aperture drilled by the implantation surgeon, and to allow for the surgical and natural morphological differences at the site of implantation encountered by the implantation surgeon during surgery. Once support shaft 10 is so inserted, stem 11 is then gripped by a gripping device and pulled with a force parallel to shaft 10, directly away from second end 5, while at the same time an opposite force, directed axially toward second end 5 of support shaft 10, is applied to support shaft 10 alone, thereby holding shaft stop 18 firmly against the outer surface of the mastoid bone implantation region 47. The force applied to pull rod stem 11 is applied in sufficient amounts to drive flared end 25 of pull rod 21 into second end 5 of support shaft 10, thereby deforming region 23 of support shaft 10 and forcing (region 23) to deform against the inner surface of the air cell-filled mastoid bone 51. Thus, a compressive connection between support shaft portion 23 and shaft stop 18 is formed, with mastoid bone therebetween. Once support shaft 10 is so securely connected to the air cell-filled region of mastoid bone 34, the implantation surgeon can continue, by attaching universal connector 6 to first end 49 of support shaft 10. As depicted in FIG. 7, a portion of pull rod stem 11 may protrude beyond the universal connector 6. At the option of the implantation surgeon, this portion of pull rod stem 11 can be removed if necessary.

Figure 12:
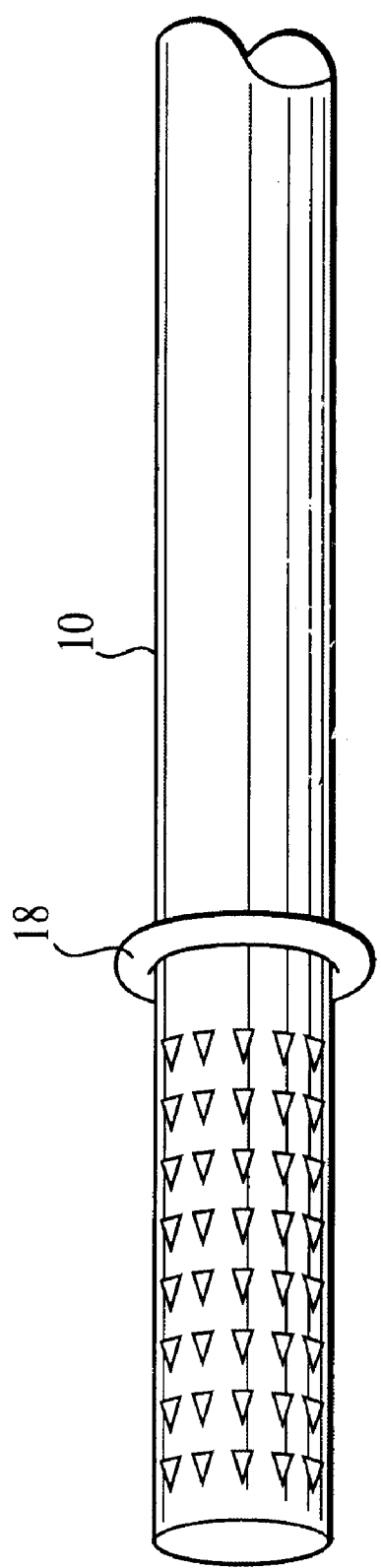
FIG. 12 is a further embodiment of the invention including one-way gripping teeth.

While the invention has been described in conjunction with specific embodiments thereof, many alternatives, modifications and variations will be apparent to those skilled in the art in light of the foregoing description. For example, the support shaft containing one-way gripping teeth 81 in FIG. 12 is an alternate means of securing the shaft within the mastoid bone containing air cells.

Accordingly, the provided invention is intended to embrace all such alternatives, modifications and variations as fall within the spirit and broad scope of the invention.

What is claimed is:

1. A support apparatus for a universal connector used in an implantable hearing assistance system, the support apparatus disposable within bone containing air cells in the middle ear region of a hearing impaired subject, the apparatus comprising:

a support shaft defining an axial bore and having a first and a second end, the first end configured to securely receive a universal connector, and the support shaft having means, disposed substantially at the second end of the support shaft, for mounting securely within the bone containing the air cells.

2. The apparatus of claim 1 wherein the means for mounting includes:

a plurality of apertures defined by the support shaft, the apertures disposed generally at the second end of the support shaft, the apertures being open to the axial bore of the support shaft; and a port defined by the support shaft, the port located substantially at the first end of the support shaft, the port open to the bore of the support shaft, and the port configured to accept injection of a sterile biocompatible adhesive, while a portion of the second end of the support shaft is disposed within the bone containing the air cells.

3. The apparatus of claim 2 wherein the port comprises a fitting disposed upon the support shaft's outer circumference substantially at the first end, the fitting defining a hole therethrough, said hole being open to the axial bore of the support shaft, the fitting configured to couple with means for injecting a sterile biocompatible adhesive therethrough.

4. The apparatus of claim 3 wherein the support shaft includes an adjustable shaft stop for limiting the depth of penetration of a portion of the second end of the support shaft into the bone containing the air cells, the adjustable shaft stop being disposable and securable upon the outer circumference of the support shaft.

5. The apparatus of claim 3 wherein the fitting is couplable to a flexible hose portion of a biocompatible adhesive pump.

6. The apparatus of claim 1 wherein the means for mounting comprises:

at least two wings, the wings having a first and second end, the first end pivotably attached substantially at the second end of the support shaft, the wings shaped to conform to the outer circumference of the support shaft when unextended, the wings being pivotably angleable while disposed within the bone containing the air cells; and an adjustable shaft stop, forcing compressive engagement between the at least two wings and the adjustable shaft stop, the bone containing the air cells being located therebetween.

7. The apparatus of claim 6 wherein the support shaft includes a threaded portion on its outer circumference to receive a retaining washer and a retaining nut configured to engage an outer surface of the bone containing the air cells, as the restraining means.

8. The apparatus of clam 6 wherein the wings are pivotable substantially from 0 to 90 degrees with respect to the plane of the support shaft.

9. The apparatus of claim 7 wherein the washer defines at least two additional apertures to receive further restraining means.

10. The apparatus of claim 1 wherein the mounting means comprises:
   a shaft stop located generally on the second end of the support shaft;
   a pull rod, substantially disposable within the bore of the support shaft, the pull rod having a stem and a head, the head disposed at a second end of the stem, the head having a diameter greater than the diameter of the second end of the support shaft, the first end of the stem extending beyond the first end of the support shaft while the head of the pull rod is engaging the second end of the support shaft; and
   a gripping means for gripping the first end of the pull rod while the pull rod is disposed within the support shaft and while the second end of the support shaft is disposed substantially within the bone containing the air cells, the gripping means configured to apply a bi-directional force upon the apparatus, the first directional force being applied to drive the pull rod axially within the support shaft bore, urging the pull rod head into engagement with the second end of the support shaft, deforming generally a portion of the second end of the support shaft, and moving the second end of the support shaft into compressive engagement with the shaft stop, the bone containing the air cells located therebetween, the second directional force directly opposing the first directional force, thereby holding the shaft stop of the support shaft in contact with the bore containing the air cells.

11. The apparatus of claim 10 wherein the shaft stop is adjustable axially along the support shaft.

12. A method of securing a support apparatus for a universal connector, used in an implantable hearing assistance system, partially within bone containing air cells in the middle ear region of a hearing impaired subject, the method comprising the steps of:
   drilling a hole in the bone containing the air cells, the hole having a radius to accommodate generally a second end of a support shaft;
   inserting the second end of the support shaft into the hole to a predetermined depth; and
   securing the generally second end of the support shaft within the bone containing the air cells.

13. The method of claim 12 wherein the securing step comprises the steps of:
   spreading at least two wings located on a second end of the support shaft, to engage an inner surface of the bone containing the air cells; and
   engaging an adjustable shaft stop on the support shaft against an outer surface of the bone containing the air cells, forming a compressive connection with the at least two wings, until the support shaft is secure.

14. The method of claim 13 wherein engaging the adjustable shaft stop comprises placing a retaining washer onto the support shaft and screwing a retaining nut over a threaded portion of the support shaft until the washer engages the bone containing the air cells, then tightening the nut so that it applies a force parallel to the support shaft sufficient to engages the at least two wings against an inner surface of the bone forming a compressive coupling to secure the position of the support shaft.

15. The method of claim 12 wherein the securing step comprises the steps of:
   injecting a sterile biocompatible glue into an aperture defined by the support shaft, located generally at a first end of the support shaft, until said biocompatible glue flows sufficiently out of a plurality of apertures located generally at a second end of the support shaft, and further until the biocompatible glue flows into and around the bone containing the air cells; and
   curing the biocompatible adhesive so as to solidify, thus securing the support shaft in position.

16. The method of claim 12 wherein the securing step comprises:
   gripping a portion of a pull rod extending beyond a first end of the support shaft;
   pulling the pull rod with a force parallel to the support shaft;
   pushing the support shaft with a force parallel to the support shaft to continually engage a shaft stop disposed on an outer circumference of the support shaft against the outer surface of bone containing air cells;
   deforming generally the second end of the support shaft against an inner portion of bone containing air cells;
   forming a compressive connection between the deformed generally second end of the support shaft and the shaft stop, with bone containing air cells therebetween, thereby securing the position of the support shaft;
   attaching a universal connector securely to a first end of the support shaft; and
   coupling a transducer to the universal connector.

* * * * *